United States Patent
Nakano

(10) Patent No.: US 9,254,497 B2
(45) Date of Patent: Feb. 9, 2016

(54) IONIZATION PROBE

(71) Applicant: SHIMADZU CORPORATION, Kyoto-shi, Kyoto (JP)

(72) Inventor: Tomohito Nakano, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/318,998

(22) Filed: Jun. 30, 2014

(65) Prior Publication Data

US 2015/0060566 A1    Mar. 5, 2015

(30) Foreign Application Priority Data

Aug. 30, 2013  (JP) ................................. 2013-179374

(51) Int. Cl.
  *H01J 49/26*   (2006.01)
  *B05B 9/00*    (2006.01)

(52) U.S. Cl.
  CPC ..................................... *B05B 9/002* (2013.01)

(58) Field of Classification Search
  USPC .......................................... 250/281, 282, 288
  See application file for complete search history.

(56) References Cited

U.S. PATENT DOCUMENTS

| | | | |
|---|---|---|---|
| 2003/0228240 A1* | 12/2003 | Dwyer | 422/99 |
| 2010/0078550 A1* | 4/2010 | Wiseman | G01N 1/405 250/282 |
| 2013/0243412 A1* | 9/2013 | Nakano | 392/485 |

FOREIGN PATENT DOCUMENTS

JP    2011-113832 A    6/2011

OTHER PUBLICATIONS

"Shimadzu Corporation Introduces the LCMS-8050 High-Sensitivity, Ultra-Fast Triple Quadrupole LC-MS/MS", http://www.shimadzu.com/an/lcms/8050/8050 2.html, Aug. 22, 2013.

* cited by examiner

*Primary Examiner* — Nicole Ippolito
(74) *Attorney, Agent, or Firm* — Sughrue Mion, PLLC

(57) ABSTRACT

In the ionization probe, an assist gas nozzle, coaxial with a nozzle, is provided around a nozzle that discharges a liquid sample. A housing inside which is formed an annular assist gas channel is provided around the assist gas nozzle. A gas inlet for introducing gas into the assist gas heating channel and gas outlet for feeding gas from channel to assist gas nozzle are provided at opposite locations across the center of the channel. Gas introduced into the assist gas heating channel is heated by a substantially annular heater, and high temperature gas is discharged through gas discharge hole of the assist gas nozzle. The heater and the channel through which high temperature gas flows are arranged solely at the tip part of the ionization probe, so thermal insulation of the probe base part can be easily accomplished.

9 Claims, 3 Drawing Sheets

IONIZATION PROBE

This application claims priority from Japan Patent Application No. 2013-79374, filed Aug. 30, 2013, the entire disclosure of which is herein incorporated by reference.

TECHNICAL FIELD

The present invention relates to an ionization probe for atomizing a liquid sample inside an ionization chamber and ionizing components in the sample; more specifically, the invention relates to an ionization probe used with ion sources in an atmospheric pressure ionization mass spectrometry apparatus which ionizes components in a liquid sample in a substantially ambient pressure atmosphere and performs mass spectrometry on the generated ions.

BACKGROUND ART

A liquid chromatography/mass spectrometry apparatus (LC/MS) generally comprises a liquid chromatograph which separates components in a sample in the time direction, and an atmospheric pressure ionization mass spectrometer which ionizes, under a substantially ambient pressure atmosphere, the components in the liquid sample eluted from the liquid chromatograph column, and performs mass analysis thereof. There are several techniques for atmospheric pressure ionization methods used to ionize the components in a liquid sample, with electrospray ionization (ESI), atmospheric pressure chemical ionization (APCI) and the like being commonly used.

Specifically, in the case of ESI, the tip of a nozzle connected to the end of the column of a liquid chromatograph is arranged facing inside an ionization chamber which has a substantially ambient pressure atmosphere, and a high voltage of about several kV is applied to the tip part of said nozzle. The liquid sample which has reached the tip part of the nozzle undergoes charge separation due to the action of the electric field generated by this high voltage and is atomized by being pulled apart mainly by Coulomb attraction. Liquid drops produced in this manner collide with air inside the ionization chamber and are reduced in size, and at the same time the solvent inside the liquid drops is vaporized. In this process, the component molecules in the liquid drops acquire an electric charge and fly out from the liquid drops, whereby gas ions are generated.

Furthermore, in the case of APCI, a needle electrode is arranged in front of a nozzle tip arranged facing inside an ionizing chamber. Carrier gas ions (buffer ions) generated by corona discharge from the needle electrode are chemically reacted with drops of liquid sample atomized by heating in the nozzle, thereby ionizing component molecules in the sample.

In this way, ESI and APCI differ in the principle of ionization, and also differ in the types of samples suitable for ionization. Thus, in common LC/MS, an ionization interface unit (hereinafter referred to as "ionization probe") is provided for APCI and for ESI, and either ionization probe can be mounted in the housing in which the ionization chamber is formed. Furthermore, ionization probes have been developed which can simultaneously perform both ESI and APCI, as described in Non-Patent Literature 1.

In an ionization probe as described above, generally, nebulizer gas, i.e. nitrogen gas or the like, is used to spray the liquid sample into the ionization chamber, but there are ionization probes known in the prior art wherein high temperature drying gas is used in addition to the nebulizer gas in order to promote the gasification of solvent from the atomized sample drops (see Patent Literature 1, etc.).

FIG. 4 is a simplified cross-sectional view of this sort of conventional ESI ionization probe.

In this ESI ionization probe 100, a narrow diameter metal narrow tube 101 through which is supplied a liquid sample eluted for example from the column outlet end of a liquid chromatograph, and a nebulizer gas tube 102 through which nebulizer gas (for example, nitrogen gas) is supplied, are formed in a coaxial double circular tube shape, and a high voltage of about several kV is applied from power supply unit 105 to the tip part of metal narrow tube 101 and nebulizer gas tube 102. Moreover, an assist gas nozzle 103a is provided further to the outside of the nebulizer gas tube 102 so as to surround the nebulizer gas tube 102, and assist gas (for example, nitrogen gas) which is heated by a heater 104 provided inside assist gas tube 103 when it passes through that tube 103 is supplied to the assist gas nozzle 103a.

Since a high voltage is applied to the tip part of the metal thin tube 101 and the nebulizer gas tube 102, a substantially annular electric insulation member 106 is arranged between the tip side (the bottom side in FIG. 4) and the base side (the top side in FIG. 4) in the nebulizer gas tube 102, and a substantially annular electric insulation member 107 is also arranged between the metal thin tube 101 and the nebulizer gas tube 102, thereby ensuring electrical insulation. The electrical insulation members 106 and 107 are members made for instance from synthetic resin or rubber.

As shown by the arrows in FIG. 4, a liquid sample is supplied to the metal narrow tube 101, and upon reaching the tip part 101a thereof, the liquid sample is charged by the action of the biased electric field formed in the vicinity of the tip end part 101a. The nebulizer gas supplied to the nebulizer gas tube 102 is discharged in the same direction as the flow of liquid sample from the nebulizer gas outlet 102a. With the assistance of nebulizer gas, the charged liquid sample turns into micro-drops and is discharged into the ionization chamber, which has a substantially ambient pressure atmosphere. The charged drops which have been thus discharged collide with the surrounding gas particles and are reduced in size, and the solvent in the drops is vaporized, in which process, ions derived from the sample components are generated.

Assist gas heated to about 400° C. to 500° C. by a heater 104 is discharged from assist gas nozzle 103a in the same direction as the flow of liquid sample and nebulizer gas. Therefore, high temperature assist gas surrounds the liquid sample spray stream, the liquid drops are efficiently heated, and gasification of solvent is promoted. As a result, ionization efficiency increases. Furthermore, the assist gas flow suppresses the spreading of the liquid sample spray stream, so the generated ions derived from the sample components can more easily reach the ion introduction unit of the mass spectrometer without scattering. As a result, more ions derived from sample components can be introduced into the mass spectrometer, for example, a quadrupole mass filter, making it possible to increase the analysis sensitivity.

PRIOR ART LITERATURES (Patent Literature 1) Japanese Unexamined Patent Application Publication 2011-113832 (Paragraph (0050), FIG. 11)
(Non-Patent Literature 1) "LCMS-2020 ultra high speed single quadrupole mass spectrometer—dual ion source DUIS-2020", Shimadzu Corporation, (retrieved Jun. 27, 2013), Internet <URL: http://www.an.shimadzu.co.jp/lcms/lcms2020/duis.htm>

In an atmospheric pressure ionization mass spectrometer, the base part of the ionization probe as described above is arranged so as to protrude to the outside of the chamber inside of which the ionization chamber is formed, and the user can adjust the amount of protrusion of the metal thin tube 101 and the nebulizer gas tube 102 from the outside. During such operation as well as during the normal execution of analysis, the user will often end up touching the base part of the ionization probe. In such cases, in order to prevent the user from sustaining burns, it is necessary to keep the temperature of the base part of the ionization probe sufficiently low to ensure safety. Furthermore, if material of low heat resistance is used as the electrical insulation members 106 and 107 for electrical insulation, the temperature of these members 106 and 107 needs to be kept below the heat resistance temperature thereof.

To this end, it is necessary to provide thermal insulation such that the heat of the high temperature assist gas and the heat of the heater 104 is not conducted to the base part of the ionization probe, and in the case of a conventional ionization probe as described above, it is necessary either to cover the entire assist gas tube 103, in which the heater 104 is housed, with a thermal insulation material so as to prevent the heat of the assist gas tube 103 heated by the heater 104 from being conducted to the nebulizer gas tube 102, or else to provide adequate space between the heated assist gas tube 103 and the nebulizer gas tube 102. However, with either of these thermal insulation methods, the size of the ionization probe inevitably increases.

The present invention was made to resolve this problem, its purpose being to provide an ionization probe which makes it possible to prevent the portions which may be touched by the user from attaining a high temperature while avoiding an increase in size.

SUMMARY OF THE INVENTION

The present invention, made to resolve the above problem, is an ionization probe for atomizing a liquid sample and ionizing components contained in said sample, characterized in that it comprises:

a) a nozzle which atomizes a liquid sample;

b) an assist gas nozzle comprising an open part provided around the tip of the aforementioned nozzle, for spraying assist gas in the same direction as the direction of atomization of liquid sample from the aforementioned nozzle;

c) an annular assist gas channel arranged so as to surround the periphery of the tip part of said assist gas nozzle and having a gas outlet which communicates with said assist gas nozzle; and d) an annular heater arranged in said assist gas channel, wherein a portion of the annular shape or in the circumferential direction of the annular heater is missing.

In the ionization probe of the present invention, the type of assist gas is not specified, but is generally an inert gas, for example, nitrogen gas or helium.

In the ionization probe of the present invention, assist gas is supplied for example from an external assist gas supply source through a suitable pipe into an annular assist gas channel provided at the tip part of the nozzle and assist nozzle. The supplied assist gas is heated by a heater in the assist gas channel and reaches a high temperature. The high temperature assist gas flows through the gas outlet of the assist gas channel into the assist gas nozzle, and is discharged through the open part provided around the nozzle tip. This high temperature assist gas stream proceeds substantially in a direction so as to surround the sample drop spray stream from the nozzle tip. Thus, the solvent in the sample drops is efficiently gasified by the heat of the assist gas. Furthermore, the spreading of the sample drop spray stream and the ions generated from those drops is suppressed.

In the ionization probe of the present invention, the heat source, including the heater and the channel through which high temperature assist gas passes, is provided only around the tip part of the nozzle which discharges sample drops into the ionization chamber, for example. Thus, the probe base part located directly at the opposite end of the ionization probe from the nozzle tip is positioned away from the heat source, and this base part is not prone to being heated and can be easily thermally insulated.

The ionization probe of the present invention is preferably configured such that the aforementioned gas outlet is formed at one circumferential location of the assist gas channel, and a gas inlet which introduces assist gas into the channel is formed at a location opposite to the gas outlet across the center of the ring of the assist gas channel. In this case, the gas inlet is suitably provided so as to introduce the assist gas in a direction substantially orthogonal to the annular assist gas channel.

In this configuration, the assist gas introduced into the assist gas channel from the gas inlet is divided in two parts, each of which passes through approximately half of the circumference of the channel and reaches the same gas outlet. The assist gas is meanwhile heated by the heater and attains a high temperature. The assist gas introduced into the assist gas channel is divided subequally into two parts, each of which is heated by substantially the same amount of heat. Thus, temperature nonuniformities of assist gas which reaches the gas outlet do not occur readily. Consequently, it becomes possible to stably discharge high temperature assist gas through the assist gas nozzle.

Furthermore, the ionization probe of the present invention is preferably configured such that the assist gas nozzle is arranged at a position offset from the center of the ring of the assist gas channel in the direction of the gas outlet.

The temperature of assist gas in the assist gas channel is higher closer to the gas outlet, and the assist gas nozzle is provided at a position near that gas outlet, so assist gas which has reached a high temperature is discharged from the open part of the assist gas nozzle without reduction in temperature. Furthermore, the assist gas nozzle is at a location far away from the gas inlet of the assist gas channel which has relatively low temperature, and thus is not readily affected by the low temperature assist gas, so the assist gas nozzle is not readily cooled. Consequently, it becomes possible to efficiently utilize the heat produced by the heater and discharge high temperature assist gas from the opening of the assist gas nozzle.

Furthermore, the ionization probe of the present invention may be suitably configured such that the heater is a micro-sheath heater, and the heater line of the micro-sheath heater is wound on both sides with the longitudinal center as a boundary, so as to form two heating parts, and the heating parts are arranged respectively in two channels extending from the gas inlet to the gas outlet within the assist gas channel.

Based on this configuration, assist gas supplied through the gas inlet to the assist gas channel and divided in two parts can be heated without nonuniformities.

It should be noted that the ionization probe of the present invention can be applied to ionization probes which perform various types of ionization wherein sample drops are sprayed from a nozzle and the components in the sample are ionized, and high temperature assist gas is employed for ionization. Typically, the present invention is especially useful for ESI ionization probes, but it can also be used for APCI ionization probes, APPI ionization probes and the like.

Furthermore, in the ionization probe of the present invention, the nozzle can be made into a coaxial double circular cylindrical tube structure with a metal thin tube forming the liquid sample channel on the inside and a nebulizer tube forming the nebulizer gas channel between itself and the outer circumferential surface of the metal thin tube on the outside. In an ESI ionization probe, a high voltage can be applied either to the metal thin tube alone or to both the metal thin tube and nebulizer tube.

With the ionization probe of the present invention, when it is mounted in an atmospheric pressure ionization mass spectrometer, the probe base part which can normally be touched by the user is located away from the heat source, making it possible to keep the probe base part at a safe temperature without using a large thermal insulation space or bulky thermal insulation material. Furthermore, since such large thermal insulation space and bulky thermal insulation material is not necessary, the size of the ionization probe itself can be reduced, which is advantageous for miniaturization of the ionization probe.

In the ionization probe of the present invention, with the preferable configurations described above, high temperature assist gas can be stably discharged from the assist gas nozzle, making it possible to promote the gasification of solvent in the sample drops and increase the ionization efficiency. Furthermore, the heat of the heater can be efficiently used, so for example, the amount of heating power necessary for discharging assist gas at the same temperature can be reduced, which is advantageous for reducing power consumption.

DETAILED DESCRIPTION OF THE EXEMPLARY EMBODIMENTS

An example of embodiment of the ionization probe of the present invention and an LC/MS in which the ionization probe of this example of embodiment has been installed will be described below with reference to the appended drawings.

Figure 1:
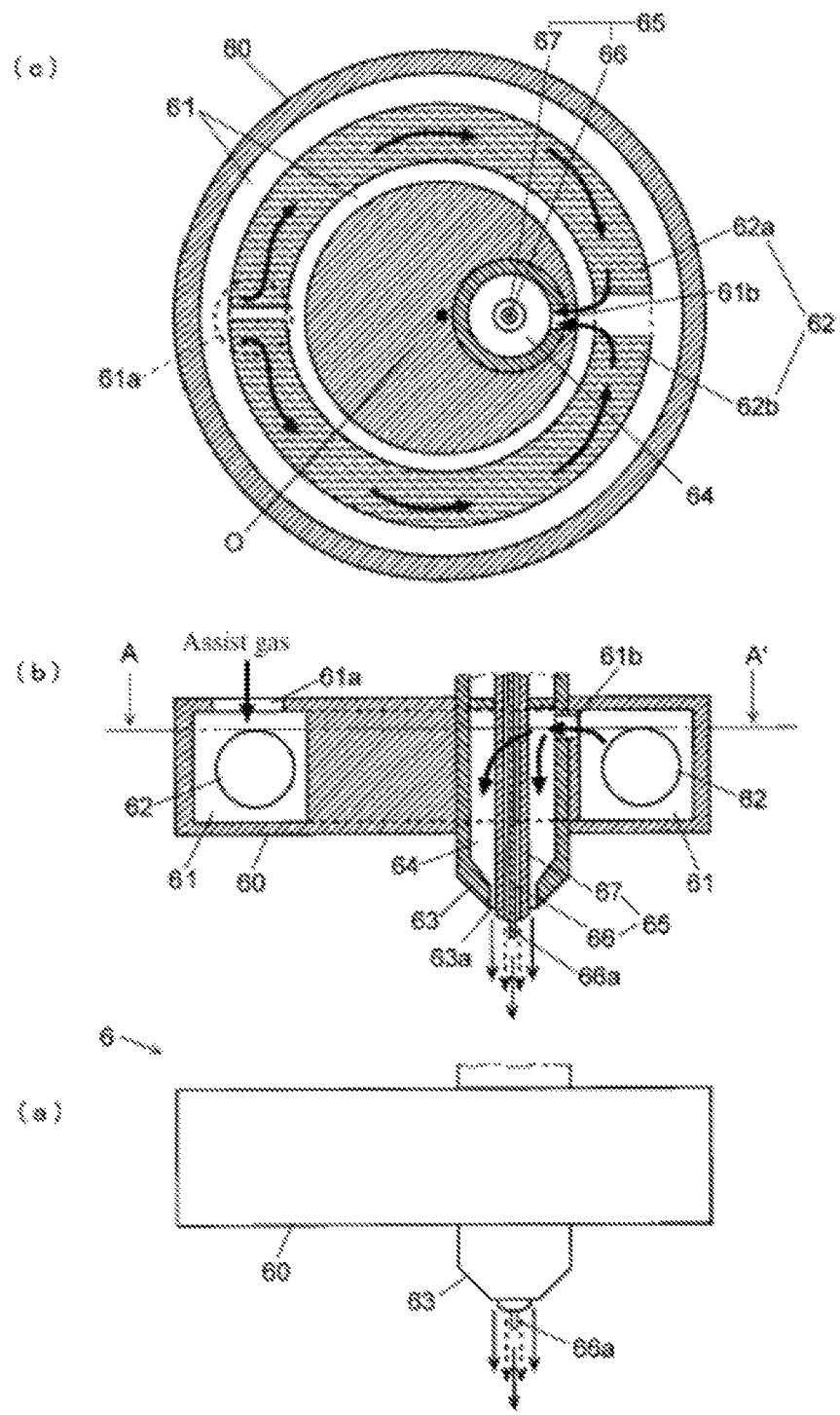
FIG. 1 is an external view of the main parts and an approximate cross-sectional diagram of an ESI ionization probe constituting an example of embodiment of the present invention.
Figure 3:
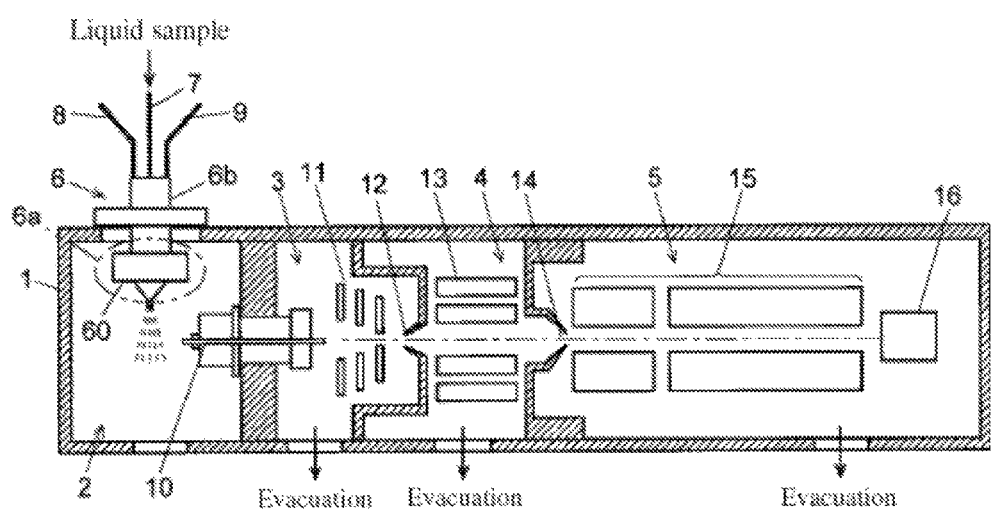
FIG. 3 is a simplified diagram of an atmospheric pressure ionization mass spectrometer in which the ionization probe of the present example of embodiment has been installed.
Figure 4:
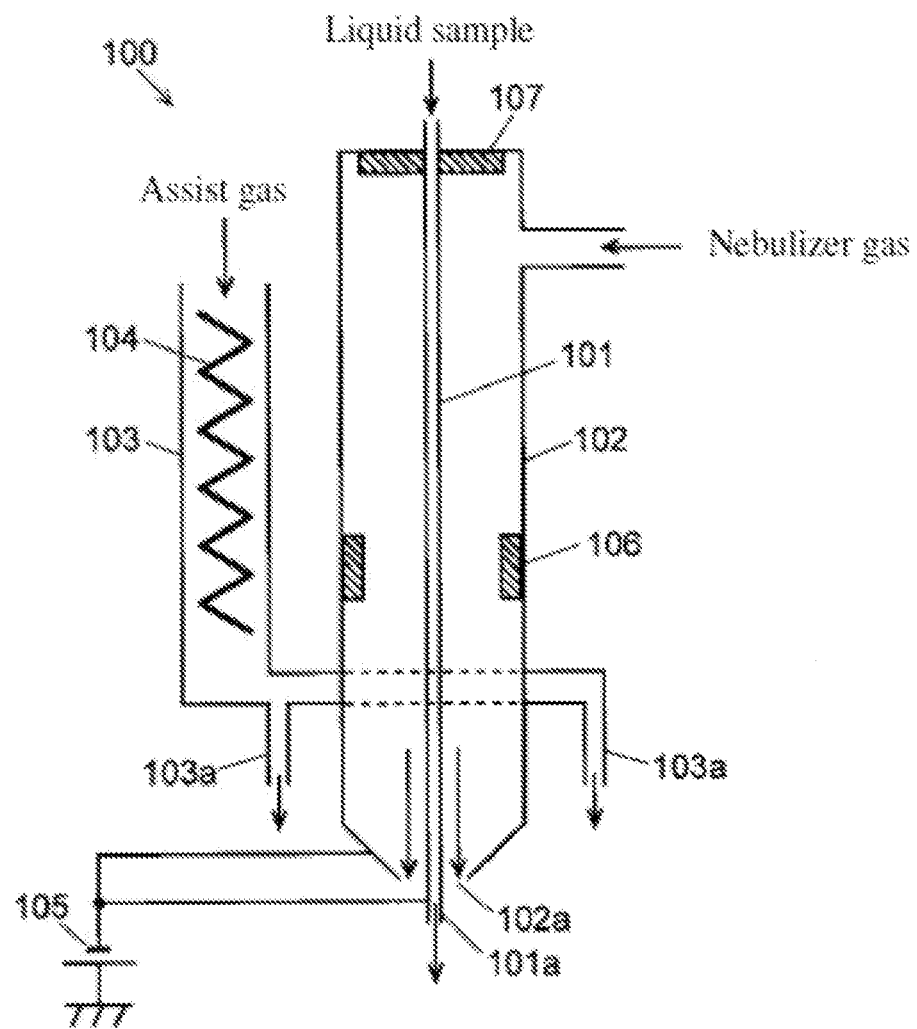
FIG. 4 is a simplified diagram of a conventional ESI ionization probe.

FIG. 1 is an external view of the main parts and an approximate cross-sectional diagram of the ESI ionization probe of the present example of embodiment, and FIG. 3 is a simplified diagram of an atmospheric pressure ionization mass spectrometer in which this ionization probe has been installed.

First, referring to FIG. 3, the atmospheric pressure ionization mass spectrometer will be described. This atmospheric pressure ionization mass spectrometer comprises, inside chamber 1, an ionization chamber 2, a first intermediate vacuum chamber 3, a second intermediate vacuum chamber 4 and an analytical chamber 5. An ESI ionization probe 6 which ionizes components in a liquid sample is arranged in ionization chamber 2, ion guides 11 and 13 which focus and transport ions are arranged respectively inside the first intermediate vacuum chamber 3 and the second intermediate vacuum chamber 4, and a quadrupole mass filter 15, which separates ions according to mass-charge ratio m/z, and an ion detector 16 are arranged inside analytical chamber 5. The ionization chamber 2 and first intermediate vacuum chamber 3 are connected via a narrow diameter heated capillary 10, the first intermediate vacuum chamber 3 and second intermediate vacuum chamber 4 are connected via an ion pass-through hole formed in the top of a skimmer 12, and the second intermediate vacuum chamber 4 and analytical chamber 5 are connected via an ion pass-through opening 14.

The inside of ionization chamber 2 has a substantially ambient pressure atmosphere, and the inside of the analytical chamber 5 is evacuated to a high vacuum of, for example, about $10^{-3}$ to $10^{-4}$ Pa with an unillustrated high performance vacuum pump. Furthermore, the first intermediate vacuum chamber 3 and second intermediate vacuum chamber 4 sandwiched between the ionization chamber 2 and analytical chamber 5 are also evacuated with a vacuum pump, forming a multistage evacuation system in which the degree of vacuum increases in stepwise fashion.

The analysis operation in this atmospheric pressure ionization mass spectrometer will be briefly explained.

A liquid sample containing components separated in the column of an unillustrated liquid chromatograph, for example, is introduced via liquid sample supply tube 7 to ESI ionization probe 6. In addition to the liquid sample, nebulizer gas and assist gas are also introduced to the ESI ionization probe 6 via nebulizer gas supply tube 8 and assist gas supply tube 9. The liquid sample is imparted with an electric charge at the tip of the ESI ionization probe 6 and is atomized inside the ionization chamber 2 with the aid of the nebulizer gas and assist gas, and the solvent in the sample drops vaporizes, in which process the sample component molecules are ionized. The generated ions, together with small drops of liquid, are drawn inside heated capillary 10 by the pressure difference between the ionization chamber 2 and the first intermediate vacuum chamber 3. While passing through the heated capillary 10, the gasification of solvent in the small drops progresses and the generation of ions is further promoted.

Ions which have passed through the heated capillary 10 and have been discharged inside the first intermediate vacuum chamber 3 are focused by the effect of the electric field formed by ion guide 11, and are introduced via the ion pass-through hole in the top of the skimmer 12 into the second intermediate vacuum chamber 4. These ions are focused by the effect of the electric field formed by ion guide 13 in the second intermediate vacuum chamber 4, and are fed via ion pass-through opening 14 toward the analytical chamber 5. In the analytical chamber 5, only ions having a specific mass-charge ratio pass through the space in the long axis direction of quadrupole mass filter 15 and reach the ion detector 16 to undergo detection. The mass-charge ratio of ions which pass through the quadrupole mass filter 15 depends on the direct current voltage and high frequency voltage applied to the quadrupole mass filter 15, so the mass-charge ratio of ions injected into ion detector 16 can be scanned across a predetermined range, for example, by scanning this applied voltage.

The ESI ionization probe 6, as described above, performs the role of ionizing components in a liquid sample under a substantially ambient pressure atmosphere, but has a distinctive structure different from the prior art. FIG. 1 (a) is an external view of the tip part 6a of the ESI ionization probe 6 shown in FIG. 3, (b) is an approximate horizontal cross-sectional view of the part shown in (a), and (c) is a cross-sectional view along line A-A' of (b).

In this ESI ionization probe 6, the nozzle 65 which atomizes the liquid sample has a coaxial double circular cylindrical structure comprising a metal thin tube 66 through which the liquid sample flows and a nebulizer gas tube 67 on the outside thereof, with the space between the outer circumference of the metal thin tube 66 and the inner circumference of the nebulizer gas tube 67 constituting a nebulizer gas channel through which nebulizer gas flows. This structure is the same as in the prior art. Furthermore, while omitted from FIG. 1, a high voltage for causing charge separation of the liquid sample is applied to both the metal thin tube 66 and the nebulizer gas tube 67, or to the metal thin tube 66 alone.

An assist gas nozzle 63, which has a circular cylindrical shape coaxial with the metal thin tube 66 and nebulizer gas tube 67, is further arranged on the outside of the nebulizer gas tube 67. The tip part of the assist gas nozzle 63 is machined into tapered shape, being made such that the assist gas is discharged in substantially the same direction as the liquid sample (charged drops) and nebulizer gas from an assist gas discharge hole 63a which opens in an annular shape.

A disc-shaped housing 60 inside which an assist gas heating channel 61 is formed is provided around the assist gas nozzle 63. A gas inlet 61a is formed at one circumferential location of the annular assist gas heating channel 61, and a gas outlet 61b which communicates with assist gas nozzle 63 is formed at a location opposite the gas inlet 61a across the center O of the disc-shaped housing 60, i.e. at a location shifted by an angle of rotation of 180° relative to the gas inlet 61a. Furthermore, in the annular assist gas heater channel 61, there is a substantially annular heater 62 which covers substantially the entire circumference thereof.

As can be seen from FIG. 1, the assist gas nozzle 63 on the inside of which the nozzle 65 is housed is arranged not at the center O of the disc-shaped housing 60 or the annular assist gas heating channel 61, but at a position offset from the center O toward the gas outlet 61b. The reason for this will be described later.

Figure 2:
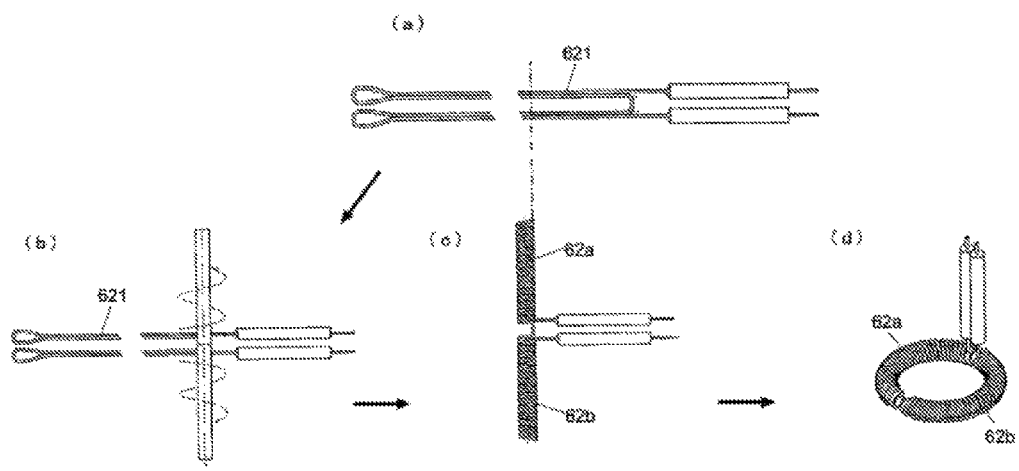
FIG. 2 is a diagram intended to explain the manufacturing procedure of the heater used in the ESI ionization probe of the present example of embodiment.

FIG. 2 is an explanatory diagram of the procedure of manufacturing the heater 62. The heater used here is a micro-sheath heater, wherein two wings of a single heater wire 621 machined approximately into a Y shape, as shown in FIG. 2 (a), are wound and thereby molded into a coil shape, as shown in FIG. 2 (b), thereby forming two heating parts 62a, 62b, as shown in FIG. 2 (c). Each heating part 62a, 62b is curved substantially into a semicircular ring shape, as shown in FIG. 2 (d), and the ends of the two heating parts 62a, 62b are brought together, thereby completing the heater 62, which consists of two substantially semicircular ring-shaped heating parts 62a and 62b.

Each of the heating parts 62a, 62b has a coil shape in which two heater wires 621 with opposite directions of current flow are integrally joined. Thus, the directions of the magnetic flux induced by the current flowing through the two closely adjacent heater wires 621 are precisely opposite directions and cancel each other out. As a result, when heating current is made to flow through the heating parts 62a, 62b, the magnetic fields induced thereby essentially pose no problem.

In this ESI ionization probe 6, the assist gas supplied through assist gas supply tube 9 is introduced through gas inlet 61a into assist gas heating channel 61. The direction of the assist gas flowing from gas inlet 61a toward assist gas heating channel 61 is substantially orthogonal to that channel 61. Moreover, the gas channel from the gas inlet 61a to the gas outlet 61b includes two channels, i.e. the upper semicircular ring-shaped channel and the lower semicircular ring-shaped channel in FIG. 1 (c), but since the channel resistance of the two channels is substantially equal, the assist gas flows in two essentially one-half portions through the two channels, upper and lower. The assist gas divided into these two parts is heated respectively by heating parts 62a and 62b of heater 62 and is combined before the gas outlet 61b and flows into the assist gas nozzle 63 through the outlet 61b. The heating parts 62a and 62b have substantially the same shape, and the quantities of assist gas flowing through the aforementioned two channels in which these heating parts are arranged are substantially equal, and thus the gas flowing through either channel is heated to substantially the same temperature. Therefore, temperature nonuniformities do not occur readily, and high temperature assist gas is stably supplied to the assist gas nozzle 63.

The assist gas which flows from the gas inlet 61a into the assist gas heating channel 61 as described above is heated as it advances toward the gas outlet 61b, so the temperature of the assist gas near the gas inlet 61a is low and the temperature of the assist gas near the gas outlet 61b is high. Since the assist gas nozzle 63 is arranged far from the gas inlet 61a and conversely near the gas outlet 61b, the assist gas which has been heated by heater 62 and reached a high temperature flows into the assist gas nozzle 63 and is discharged from assist gas discharge hole 63a essentially without being cooled. Furthermore, the assist gas nozzle 63 is located away from the assist gas heating channel 61 near the gas inlet 61a where relatively low temperature assist gas is present, so the assist gas nozzle 63 itself is also not readily cooled. Thus, the heat generated by the heater 62 can be utilized without waste and stable high temperature assist gas can be discharged from the assist gas discharge hole 63a.

Charged drops derived from the liquid sample discharged from the tip of the nozzle 65 receive the heat of the assist gas flowing in substantially the same direction so as to surround the drops, and the solvent in the drops is rapidly gasified. As a result, the sample components in the drops are efficiently ionized. Furthermore, spreading of the liquid drop spray stream and spreading of the ions generated therefrom is suppressed. Ions derived from sample components thus do not scatter readily mid-way, and efficiently reach the ion introduction unit (the entry end of heated capillary 10 in FIG. 3). As a result, the quantity of ions made available for mass analysis increases, and the analysis sensitivity can be increased.

As shown in FIG. 1 and FIG. 3, in this ESI ionization probe 6, the heat source, such as the heater 62 and the channel through which heated high-temperature assist gas flows, is arranged solely in the tip part 6a. Thus, the probe base part 6b, which can be easily touched by the user during execution of analysis and during operations such as connecting the liquid sample supply tube 7 and the like, adjusting the amount of protrusion of the metal thin tube 66 in the probe tip part 6a, etc., is located away from the heat source. Thus, the probe base part 6b is not heated readily and there is no need to use bulky thermal insulating material when providing thermal insulation.

In the above example of embodiment, a case was described wherein the present invention was applied to an ESI ionization probe, but it is obvious that the present invention can also be applied to ionization probes for APCI and other atmospheric pressure ionization methods, for example, atmospheric pressure photoionization (APPI).

Furthermore, the above example of embodiment is one example of the present invention, and any alterations, modifications, additions, etc. within the gist of the present invention are obviously also included within the scope of patent claims of the present application.

EXPLANATION OF REFERENCES

6 . . . ESI ionization probe
6a . . . Probe tip part
6b . . . Probe base part
60 . . . Disc-shaped housing
61 . . . Assist gas heating channel
61a . . . Gas inlet
61b . . . Gas outlet
62 . . . Heater
621 . . . Heater wire
62a, 62b . . . Heating part
63 . . . Assist gas nozzle
63a . . . Assist gas discharge hole
65 . . . Nozzle
66 . . . Metal thin tube
67 . . . Nebulizer gas tube
7 . . . Liquid sample supply tube
8 . . . Nebulizer gas supply tube
9 . . . Assist gas supply tube

What is claimed is:

1. An ionization probe for atomizing a liquid sample and ionizing components contained in said sample, comprising:
   a) a nozzle which atomizes a liquid sample;
   b) an assist gas nozzle comprising an open part provided around the tip of the aforementioned nozzle, for spraying assist gas in the same direction as the direction of atomization of liquid sample from the aforementioned nozzle;
   c) an annular assist gas channel arranged so as to surround the periphery of the tip part of said assist gas nozzle and having a gas outlet which communicates with said assist gas nozzle; and
   d) an annular heater arranged in said annular assist gas channel, wherein at least one portion of the annular shape or in the circumferential direction of the annular heater is missing;
   wherein the at least one missing portion of the annual heater is aligned with a gas inlet gas inlet which admits assist gas into said annular assist gas channel and is aligned with the gas outlet which communicates with said assist gas nozzle.

2. The ionization probe as described in claim 1, wherein said gas outlet is formed at one circumferential location of said annular assist gas channel, the at least one missing portion of the annual heater comprises two portions, and the gas inlet which admits assist gas into said annular assist gas channel is formed at a position opposite said gas outlet across the center of the ring of said channel.

3. The ionization probe as described in claim 2, wherein said heater is a micro-sheath heater, the heater line of said micro-sheath heater is wound on both sides with the longitudinal center as a boundary, so as to form two heating parts, and said heating parts are arranged respectively in two channels extending from said gas inlet to said gas outlet within said annular assist gas channel.

4. The ionization probe as described in claim 2, wherein said assist gas nozzle is provided at a location displaced from the center of the ring of said annular assist gas channel in the direction of said gas outlet.

5. The ionization probe as described in claim 4, wherein said heater is a micro-sheath heater, the heater line of said micro-sheath heater is wound on both sides with the longitudinal center as a boundary, so as to form two heating parts, and said heating parts are arranged respectively in two channels extending from said gas inlet to said gas outlet within said annular assist gas channel.

6. The ionization probe as described in claim 1, wherein said assist gas nozzle is provided at a location displaced from the center of the ring of said annular assist gas channel in the direction of said gas outlet.

7. The ionization probe as described in claim 6, wherein said heater is a micro-sheath heater, the heater line of said micro-sheath heater is wound on both sides with the longitudinal center as a boundary, so as to form two heating parts, and said heating parts are arranged respectively in two channels extending from said gas inlet to said gas outlet within said annular assist gas channel.

8. The ionization probe as described in claim 1, wherein said assist gas nozzle surrounds said nozzle, and said annular assist gas channel surrounds said assist gas nozzle.

9. The ionization probe as described in claim 1, wherein said assist gas which introduced from the gas inlet flows circumferentially inside of said annular assist gas channel.

* * * * *